US00PP37517P2

(12) United States Plant Patent
van Veen

(10) Patent No.: US PP37,517 P2
(45) Date of Patent: Jul. 7, 2026

(54) ***ASTILBE* PLANT NAMED 'VISION IN WHITE DELIGHT'**

(50) Latin Name: ***Astilbe* x *arendsii***
Varietal Denomination: Vision in White Delight

(71) Applicant: Wilhelmus Franciscus van Veen, Erica (NL)

(72) Inventor: Wilhelmus Franciscus van Veen, Erica (NL)

(73) Assignee: FUTURE PLANTS LICENTIE B.V., Hillegom (NL)

( * ) Notice: Subject to any disclaimer, the term of this patent is extended or adjusted under 35 U.S.C. 154(b) by 0 days.

(21) Appl. No.: 19/257,689

(22) Filed: Jul. 2, 2025

(51) Int. Cl.
*A01H 5/02* (2018.01)
*A01H 5/12* (2018.01)
*A01H 6/80* (2018.01)

(52) U.S. Cl.
USPC ..... Plt./407
CPC ..... *A01H 6/80* (2018.05); *A01H 5/02* (2013.01); *A01H 5/12* (2013.01)

(58) Field of Classification Search
USPC ..... Plt./407
CPC ..... A01H 5/02; A01H 5/00; A01H 6/80
See application file for complete search history.

(56) References Cited

PUBLICATIONS

Community Plant Variety Office Version 4.23.12, retrieved on Oct. 14, 2025 at https://online.plantvarieties.eu/publicConsultation Details?registerId=20241191&denomination=vision%20in%20white%20delight, 2 pp. (Year: 2025).*
Jansen's Overseas Catalogue 2025, retrieved on Oct. 14, 2025 at https://www.jansensoverseas.com/bestanden/Catalogue_with_images_2025_spring-summer_products.pdf, pp. 1-16. (Year: 2025).*
The National Gardening Association Plant Database, retrieved on Oct. 14, 2025 at https://garden.org/plants/view/124375/Astilbe-Weisse-Gloria/, 4 pp. (Year: 2025).*

* cited by examiner

*Primary Examiner* — June Hwu
(74) *Attorney, Agent, or Firm* — C. Anne Whealy

(57) ABSTRACT

A new and distinct cultivar of *Astilbe* plant named 'Vision in White Delight', characterized by its upright plant habit with numerous erect inflorescences; dark green-colored leaves; freely and uniformly flowering habit; long flowering period; white-colored flowers on strong peduncles; and good garden performance.

2 Drawing Sheets

Figure 1:
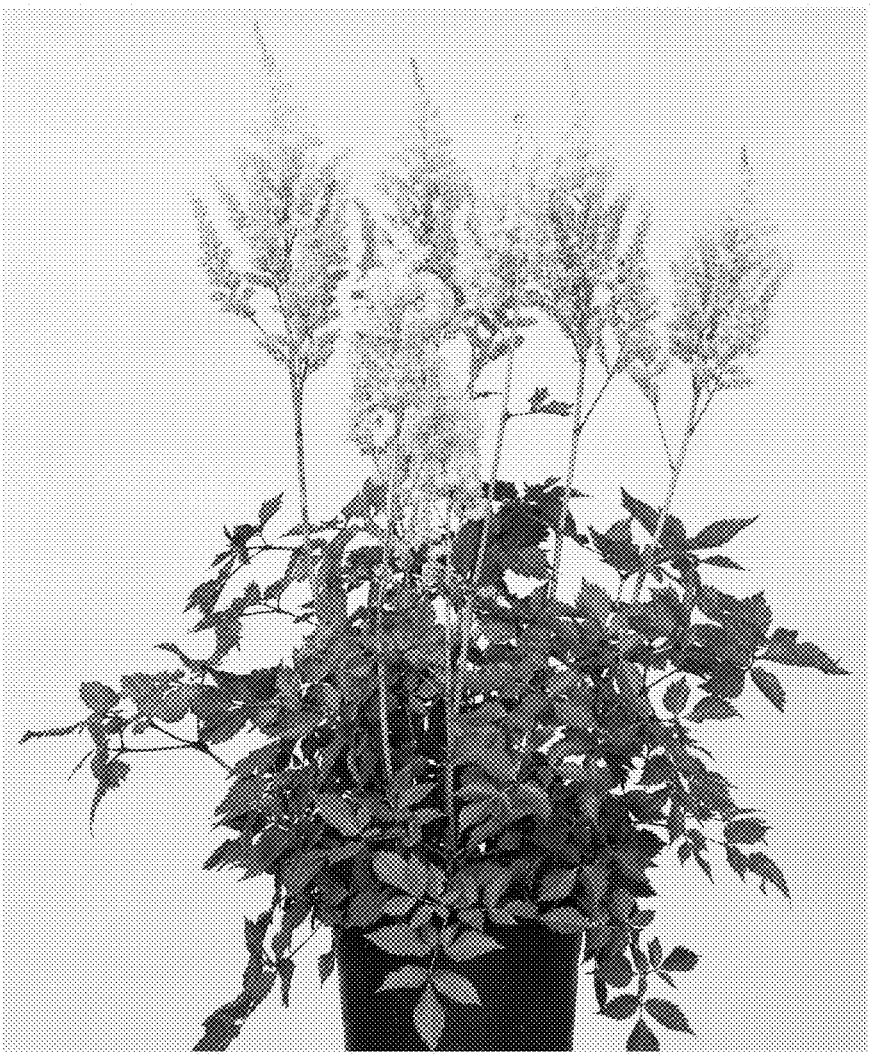

Botanical designation: *Astilbe* x *arendsii*.
Cultivar denomination: 'VISION IN WHITE DELIGHT'.

BACKGROUND OF THE INVENTION

The present invention relates to a new and distinct cultivar of *Astilbe,* botanically known as *Astilbe* x *arendsii* and hereinafter referred to by the name 'Vision in White Delight'.

The new *Astilbe* plant is a product of a planned breeding program conducted by the Inventor in Erica, The Netherlands. The objective of the breeding program was to create new uniform and freely flowering *Astilbe* plants with attractive leaf and flower coloration.

The new *Astilbe* plant originated from a cross-pollination conducted by the Inventor in June 2018 in Erica, The Netherlands, of an unnamed seedling selection of *Astilbe* x *arendsii,* not patented, as the female, or seed, parent with *Astilbe* x *arendsii* 'Weisse Gloria', not patented, as the male, or pollen, parent. The new *Astilbe* plant was discovered and selected by the Inventor as a single flowering plant from within the progeny of the stated cross-pollination in a controlled greenhouse environment in Erica, The Netherlands in June 2021.

Asexual reproduction of the new *Astilbe* plant by vegetative divisions in a controlled nursery environment in Erica, The Netherlands since June 2021, has shown that the unique features of this new *Astilbe* plant are stable and reproduced true to type in successive generations.

SUMMARY OF THE INVENTION

Plants of the new *Astilbe* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Vision in White Delight'. These characteristics in combination distinguish 'Vision in White Delight' as a new and distinct *Astilbe* plant:

1. Upright plant habit with numerous erect inflorescences.
2. Dark green-colored leaves.
3. Freely and uniformly flowering habit.
4. Long flowering period.
5. White-colored flowers on strong peduncles.
6. Good garden performance.

Plants of the new *Astilbe* differ primarily from plants of the female parent selection in the following characteristics:

1. Leaves of plants of the new *Astilbe* are smaller and darker green in color than leaves of plants of the female parent selection.

2. Plants of the new *Astilbe* flower about two weeks earlier than plants of the female parent selection.

Plants of the new *Astilbe* can be compared to plants of the male parent, 'Weisse Gloria'. In side-by-side comparisons, plants of the new *Astilbe* and 'Weisse Gloria' differ primarily in the following characteristics:

1. Plants of the new *Astilbe* produce more inflorescences per plant than plants of 'Weisse Gloria'.
2. Inflorescences of plants of the new *Astilbe* have more flowers per inflorescence than inflorescences of plants of 'Weisse Gloria'.
3. Plants of the new *Astilbe* have smaller flowers than plants of 'Weisse Gloria'.
4. Plants of the new *Astilbe* flower have finer pedicels than plants of 'Weisse Gloria'.

Plants of the new *Astilbe* can be compared to plants of *Astilbe chinensis* 'Vision in White', disclosed in U.S. Plant Pat. No. 18,965. In side-by-side comparisons, plants of the new *Astilbe* and 'Vision in White' differ primarily in the following characteristics:

1. Root systems of plants of the new *Astilbe* are more vigorous than root systems of plants of 'Vision in White'.
2. Plants of the new *Astilbe* flower about two weeks earlier than plants of 'Vision in White'.
3. Plants of the new *Astilbe* produce more inflorescences per plant than plants of 'Vision in White'.
4. Inflorescences of plants of the new *Astilbe* have more flowers per inflorescence than inflorescences of plants of 'Vision in White'.
5. Plants of the new *Astilbe* have smaller flowers than plants of 'Vision in White'.
6. Plants of the new *Astilbe* flower have finer pedicels than plants of 'Vision in White'.

BRIEF DESCRIPTION OF THE PHOTOGRAPHS

The accompanying colored photographs illustrate the overall appearance of the new *Astilbe* plant showing the colors as true as it is reasonably possible to obtain in colored reproductions of this type. Colors in the photographs may differ slightly from the color values cited in the detailed botanical description which accurately describe the colors of the new *Astilbe* plant.

The photograph on the first sheet (FIG. 1) is a side perspective view of a typical flowering plant of 'Vision in White Delight' grown in a container.

Figure 2:
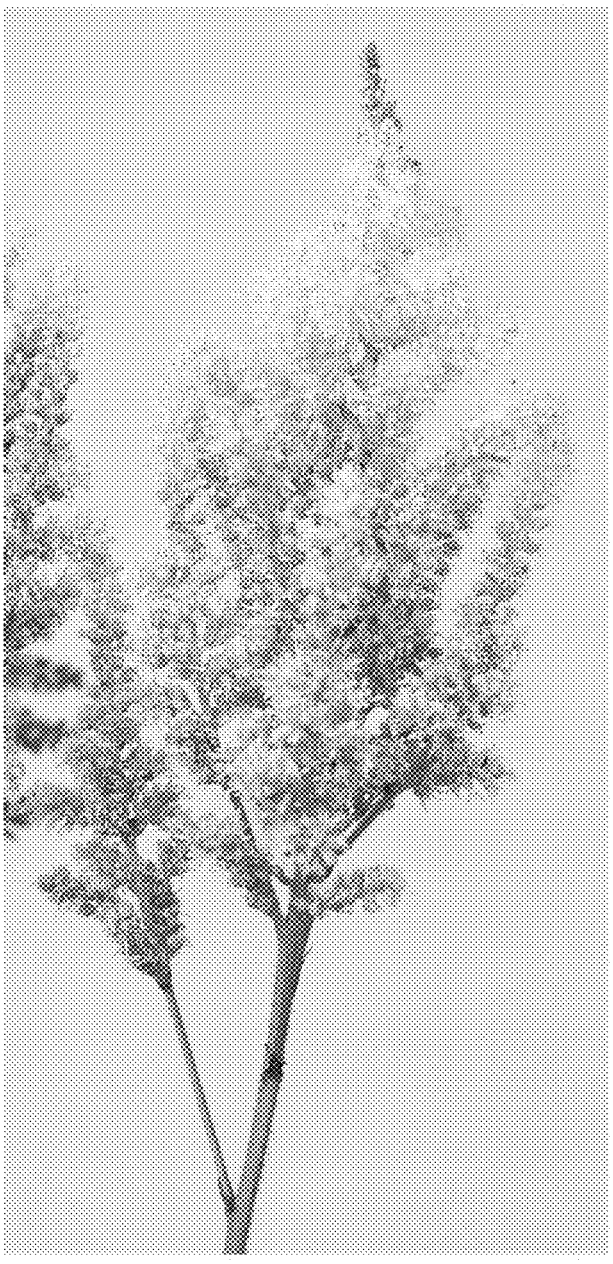

The photograph on the second sheet (FIG. 2) is a close-up view of typical inflorescences of 'Vision in White Delight'.

DETAILED BOTANICAL DESCRIPTION

The aforementioned photographs and following observations, measurements and values describe plants grown during the summer in 15-cm containers in an outdoor nursery in Erica, The Netherlands and under cultural practices typical of commercial *Astilbe* production. During the production of the plants, day temperatures ranged from 18° C. to 30° C. and night temperatures ranged from 10° C. to 20° C. Plants were two years old when the photographs and description were taken. In the following description, color references are made to The Royal Horticultural Society Colour Chart, 2015 Edition, except where general terms of ordinary dictionary significance are used.

Botanical classification: *Astilbe* x *arendsii* 'Vision in White Delight'.

Parentage:

*Female, or seed, parent*.—Unnamed seedling selection of *Astilbe* x *arendsii,* not patented.

*Male, or pollen, parent*.—*Astilbe* x *arendsii* 'Weisse Gloria', not patented.

Propagation:

*Type*.—By vegetative divisions.

*Time to initiate roots*.—About 30 days at temperatures about 18° C.

*Time to produce a rooted young plant*.—About eight months at temperatures about 20° C.

*Root description*.—Fine, moderately fibrous; typically white to greyed-orange in color, actual color of the roots is dependent on substrate composition, water quality, fertilizer type and formulation.

*Rooting habit*.—Freely branching; medium density.

Plant description:

*Plant form and growth habit*.—Herbaceous perennial; upright plant habit with numerous erect inflorescences with inflorescences held above the foliar plane on strong peduncles; flowering stems and leaves basal; freely flowering with numerous basal branches developing per plant, dense and bushy appearance; moderately vigorous growth habit; moderate growth rate; and freely and uniformly flowering habit.

*Growth rate*.—Moderately rapid; from rooted young plants, about three months are required to produce fully-grown flowering plants in containers.

*Plant height* (*soil level to top of foliar plane*).—About 27.9 cm.

*Plant height* (*soil level to top of inflorescences*).—About 54 cm.

*Plant width* (*spread*).—About 41.8 cm.

*Stem description*.—Quantity per plant: About eight basal branches per plant. Length: About 21.7 cm. Diameter: About 4 mm. Internode length: About 10.4 cm. Strength: Strong. Aspect: Erect to about 10° from vertical. Texture and luster: Moderately pubescent; pubescence minute and strigose; slightly glossy. Color, developing: Close to 144B. Color, at the internodes: Varying from close to 182A to 182D. Color, developed: Close to 144B.

Leaf description:

*Arrangement*.—Alternate; biternately compound; on average, about 23 leaflets per leaf.

*Leaf length* (*excluding petiole*).—About 16.6 cm.

*Leaf width*.—About 14.7 cm.

*Terminal leaflet length*.—About 4.9 cm.

*Terminal leaflet width*.—About 2.7 cm.

*Lateral leaflet length*.—About 3.9 cm.

*Lateral leaflet width*.—About 2.1 cm.

*Leaf shape, in outline*.—Broadly ovate to broadly rhomboidal.

*Leaflet shape*.—Elliptic to ovate.

*Leaflet apex*.—Narrowly acute.

*Leaflet base*.—Attenuate to narrowly cuneate; occasionally, obtuse.

*Leaflet margin*.—Biserrate; not lobed.

*Leaflet texture and luster, upper and lower surfaces*.—Lamina, smooth; along the midvein and lateral venation, moderately pubescent; semi-glossy.

*Leaflet venation pattern*.—Pinnate.

*Leaflet color*.—Developing leaflets, upper surface: Close to 143B to 143C; narrow marginal edges, close to 172B. Developing leaflets, lower surface: Close to 143C; narrow marginal edges, close to 172C. Fully expanded leaflets, upper surface: Close to NN137B; marginal apices, close to 174A; venation, close to N144A. Fully expanded leaflets, lower surface: Close to 147B; marginal apices, close to 174A; venation, close to 150D.

*Leaf petiole length*.—About 17.5 cm.

*Leaf petiole diameter*.—About 2 mm.

*Leaf and leaflet petiole strength*.—Strong.

*Leaf and leaflet petiole texture and luster, upper and lower surfaces*.—Moderately pubescent; semi-glossy.

*Leaf and leaflet petiole color, upper surface*.—Close to 151A; fading proximally to closer to 146C; at the nodes, close to 178A.

*Leaf and leaflet petiole color, lower surface*.—Close to 150C; fading proximally to closer to 146C to 146D; at the nodes, close to 146D.

Flower description:

*Flower type and flowering habit*.—Single rotate flowers arranged on erect terminal compound panicles; flowers face upright, outward or downward depending on position on the inflorescence; panicles conical in shape; freely and uniformly flowering habit with about 3,000 flowers developing per inflorescence and about 27,000 flowers developing per plant during the flowering season.

*Fragrance*.—Faintly fragrant; moldy-sweet, pleasant.

*Natural flowering season*.—Plants begin flowering about three months after planting rooted young plants; continuously flowering from late spring until late summer in The Netherlands.

*Postproduction longevity*.—Individual flowers last about ten days on the plant; flowers not persistent.

*Flower buds*.—Height: About 1.5 mm. Diameter: About 1.5 mm. Shape: Roughly spherical. Texture and luster: Smooth, glabrous; matte. Color: Sepals, close to 145A and petals, close to NN155A with apices, tinged with close to 73C.

*Inflorescence height*.—About 26.3 cm.

*Inflorescence diameter*.—About 10.8 cm.

*Flower diameter*.—About 6 mm by 6 mm.

*Flower depth*.—About 4 mm.

*Petals*.—Quantity per flower: Typically five in a single whorl. Length: About 4 mm. Width: About 0.8 mm. Shape: Oblanceolate. Apex: Obtuse. Base: Narrowly cuneate. Margin: Entire; not undulate. Texture and luster, upper and lower surfaces: Smooth, glabrous; matte. Color: Developing petals, upper and lower surfaces: Close to NN155D. Fully expanded petals, upper and lower surfaces: Close to NN155D; color does not change with subsequent development.

*Sepals*.—Quantity per flower: Typically five in a single whorl; towards the base forming a campanulate-shaped calyx. Calyx length: About 2 mm. Calyx diameter: About 2.5 mm. Length: About 2 mm. Width: About 0.8 mm. Shape: Ovate. Apex: Obtuse. Base: Cuneate, fused. Margin: Entire. Texture and luster, upper and lower surfaces: Smooth, glabrous; matte. Color: Developing sepals, upper surface: Close to 155C to 155D; towards the apex, tinged with close to 63C. Developing sepals, lower surface: Close to 155C to 155D. Fully expanded sepals, upper and lower surfaces: Close to 155D; color does not change with subsequent development.

*Peduncles*.—Length: About 25.7 cm. Diameter: About 3 mm. Angle: Primary peduncles, mostly erect; lateral peduncles, about 32.5° to primary peduncle axis. Strength: Strong. Texture and luster: Densely pubescent; semi-glossy. Color: Close to 144B.

*Pedicels*.—Length: About 1 mm. Diameter: About 0.5 mm. Angle: About 45° from peduncle axis. Strength: Moderately strong. Texture and luster: Moderately pubescent; matte. Color: Close to 155C.

*Reproductive organs*.—Stamens: Quantity per flower: Typically ten. Filament length: About 3 mm. Filament color: Close to NN155D. Anther shape: Broadly ovate. Anther size: About 0.5 mm by 0.3 mm. Anther color: Close to 155D. Pollen amount: Scarce. Pollen color: Close to NN155A. Pistils: Quantity per flower: Two. Pistil length: About 1 mm. Stigma diameter: About 0.25 mm. Stigma shape: Club-shaped. Stigma color: Close to 155C. Style length: About 0.8 mm. Style color: Close to 155C. Ovary color: Close to 155C.

*Seeds and fruits*.—To date, seed and fruit development have not been observed on plants of the new *Astilbe*.

Pathogen & pest resistance: To date, plants of the new *Astilbe* have not been noted to be resistant to pathogens and pests common to *Astilbe* plants.

Garden performance: Plants of the new *Astilbe* have been observed to have good garden performance and tolerate rain, wind, temperatures ranging from about −25° C. to 35° C. and to be suitable for USDA Hardiness Zones 5 through 10.

It is claimed:

1. A new and distinct *Astilbe* plant named 'Vision in White Delight' as herein illustrated and described.

* * * * *